United States Patent
Huang et al.

(10) Patent No.: US 11,996,663 B2
(45) Date of Patent: May 28, 2024

(54) BONDING DEVICE, BONDING STRUCTURE FOR WEARABLE DEVICE AND NODE DEVICE FOR FORMING SENSING POINT ON SIGNAL CONNECTING LINE THEREOF

(71) Applicant: J-MEX Inc., Hsinchu (TW)

(72) Inventors: Chun-Yuan Huang, Hsinchu (TW); Wei-Chun Hsueh, Hsinchu (TW)

(*) Notice: Subject to any disclaimer, the term of this patent is extended or adjusted under 35 U.S.C. 154(b) by 1038 days.

(21) Appl. No.: 16/825,166

(22) Filed: Mar. 20, 2020

(65) Prior Publication Data
US 2021/0135416 A1    May 6, 2021

(51) Int. Cl.
| | |
|---|---|
| H01R 33/92 | (2006.01) |
| A61B 5/00 | (2006.01) |
| A61B 5/11 | (2006.01) |
| A61B 5/251 | (2021.01) |
| A61B 5/256 | (2021.01) |
| A61B 5/257 | (2021.01) |
| A61H 1/02 | (2006.01) |

(52) U.S. Cl.
CPC ............. *H01R 33/92* (2013.01); *A61B 5/11* (2013.01); *A61B 5/1114* (2013.01); *A61B 5/251* (2021.01); *A61B 5/256* (2021.01); *A61B 5/257* (2021.01); *A61B 5/6804* (2013.01); *A61B 5/6824* (2013.01); *A61B 2560/0443* (2013.01); *A61H 1/0274* (2013.01)

(58) Field of Classification Search
CPC .. A61B 5/11; A61B 5/1114; A61B 2560/0443
See application file for complete search history.

(56) References Cited

U.S. PATENT DOCUMENTS

| | | | | |
|---|---|---|---|---|
| 5,252,091 | A * | 10/1993 | Fujita | H01R 25/14 439/499 |
| 7,462,035 | B2 * | 12/2008 | Lee | H01R 12/592 439/37 |
| 8,214,007 | B2 * | 7/2012 | Baker | A61B 5/14552 600/382 |
| 9,504,396 | B2 * | 11/2016 | Korkala | A61B 5/25 |
| 9,775,561 | B2 * | 10/2017 | Russell | A61B 5/0024 |
| 9,795,299 | B2 * | 10/2017 | Russell | A61B 5/274 |
| 10,367,300 | B2 * | 7/2019 | Shedletsky | G04G 17/04 |
| 10,768,581 | B2 * | 9/2020 | Wang | G04G 17/04 |
| 11,092,933 | B2 * | 8/2021 | Thomas | G04G 17/06 |

(Continued)

*Primary Examiner* — Neil Abrams

(57) ABSTRACT

A bonding device for a wearable device includes a first bonding structure and a second bonding structure. The first bonding structure includes a first wire connecting member, a first bonding member and an elastic member, and has a plurality of first mechanical structures configured to form a first mechanical bond and a plurality of first electrical contacts configured to form a first electrical bond, and the second bonding structure includes a first signal connecting line, wherein the first wire connecting member, the first bonding member, and the elastic member form the first mechanical bond through the plurality of first mechanical structures; the first wire connecting member, the first bonding member, and the elastic member form the first electrical bond through the plurality of first electrical contacts; and the elastic member is electrically connected to the first signal connecting line to combine the first bonding structure and the second bonding structure.

20 Claims, 13 Drawing Sheets

(56) References Cited

U.S. PATENT DOCUMENTS

| | | | |
|---|---|---|---|
| 2017/0319132 A1* | 11/2017 | Longinotti-Buitoni | ................... |
| | | | G16H 40/67 |
| 2021/0135416 A1* | 5/2021 | Huang | ................ A61B 5/1114 |
| 2021/0296834 A1* | 9/2021 | Huang | ................ B25J 9/0006 |

* cited by examiner

BONDING DEVICE, BONDING STRUCTURE FOR WEARABLE DEVICE AND NODE DEVICE FOR FORMING SENSING POINT ON SIGNAL CONNECTING LINE THEREOF

CROSS REFERENCE TO RELATED APPLICATION

This application claims the benefit of Taiwan's Patent Application No. 108214331, filed on Oct. 30, 2019, at Taiwan's Intellectual Property Office, the disclosures of which are incorporated herein in their entirety by reference.

TECHNICAL FIELD

Embodiments of the present disclosure are related to a bonding device, a bonding structure, a signal connecting line, and a node device for a wearable device, and more particularly, are related to a sensing module and a signal processing module for a bonding device, a bonding structure, a signal connecting line, and a node device of the wearable device thereof.

BACKGROUND

Due to the development of technology and the advancement of communication technology, high-speed signal transmission scheme with low latency enable various electronic devices to communicate with each other, and the electronic devices can transfer data to the cloud server for processing, that is, the Internet of Things (IoT) can be implemented. By means of machine learning, deep learning and big data analysis, the cloud server can analyze these data, make decisions by using artificial intelligence (AI) and even predict the occurrence of events. In the fields of health, medical rehabilitation, elderly care, entertainment, virtual reality, etc., various sensors can be used to generate various physiological or motion data on the human body to monitor the state of the human body in real time, and transmit the data to the cloud server for analysis in order to monitor an individual's health, medical treatment and care, or to achieve the efficacies of preventive medicine and health care. The physiological data or exercise data generated by these sensors can also be used in various virtual realities.

The motion state of the human body can be detected by locating motion sensors on the limbs and the trunk. A costume worn on the user, having motion sensors attached thereon is a convenient way to locate the motion sensors on the human body. In general, the sensors on the costume—the wearable device are wired to transmit the sensing signals resulting from sensors sensing the human body motion including joints bending, limbs stretching or contracting. The wires connecting to the sensors must be flexible to adapt to the body in motion and connecting firmly to the sensor attached on the costume put on the body to transmit the sensed physiological signal for processing. However, in some prior-art wearable devices or equipment, the sensor is connected through the general-purpose electric wires without a flexibility arrangement to accommodate the limb in motion. Though, the prior art, the published patent application with No. US20170319132 disclosing a physiological monitoring method adopting wavy wires sewn on the garment, to transmit the signal of the sensor thereon, the prior art does not disclose a structure or a device to accommodate the wavy wires in an integration configuration comprising a mechanical bonding and an electrical bonding to perform the wires flexibility to responding to the body or limbs in motion and transmit reliably the signal.

However, in the present invention a configuration that integrates signal wires, motion sensors, processing modules and fabrics is disclosed, the motion sensors and the processing modules are connected to each other via the wavy signal wires embedded in the fabric to form a suite of wearable devices the costume, which can be worn on different limbs or trunk of user's body for body motion sensing.

SUMMARY OF INVENTION

In view of the drawback in the above-mentioned prior art, the present invention proposes a bonding structure, a structural object or a bonding device for forming a suite of wearable devices, which includes a first bonding structure having a first signal connecting line and a second bonding structure having a second signal connecting line. The first and the second bonding structures are configured to form a combination structure, the structural object or the bonding device. Each of the first and the second bonding structures has a plurality of corresponding mechanical structures and a plurality of electrical contacts to form a mechanical bonding and an electrical bonding. The first bonding structure includes a first rigid unit having a sensing module, a first pivot connecting member and a first bonding member; and three of them are configured to form a first mechanical bonding by using a plurality of corresponding first mechanical structures, and to form a first electrical bonding by using a plurality of corresponding first electrical contacts. The second bonding structure includes a second rigid unit having a processing module, a second pivot connecting member and a second bonding member; and three of them are configured to form a second mechanical bonding by using a plurality of corresponding second mechanical structures, and to form a second electrical bonding by using a plurality of corresponding second electrical contacts.

Each of the pivot connecting members may be a wire connecting member, which may be combined with an elastic fabric and a sensing module having a plurality of flexible wires. The bonding member can be used to combine the pivot connecting member, the elastic fabric, and the sensing module to form a bonding structure for sensing the motion state of the user's limb or body. The pivot connecting member includes a plurality of connectors, each of which can be a concave or an indentation shape and includes an upper connector and a lower connector. Each of the upper and the lower connectors has a left side hole and a right side hole to bond with the bonding member mechanically. The upper connector and the lower connector may form a slot; and the plurality of flexible wires form a linear shape at its electrical connection portion where the pivot connecting member is bonded. Each of the flexible wires is embedded into each of the slots to form the electrical bonding. The upper and the lower connectors have an upper hole and a lower hole respectively, for electrically connecting the pivot connecting member with the sensing module.

In accordance with one embodiment of the present disclosure, a bonding device for a wearable device is provided. The bonding device for a wearable device includes a first bonding structure and a second bonding structure. The first bonding structure includes a first wire connecting member, a first bonding member and an elastic member. The first bonding structure has a plurality of first mechanical structures configured to form a first mechanical bond and a plurality of first electrical contacts configured to form a first electrical bond, and the second bonding structure includes a first signal connecting line, wherein the first wire connecting member, the first bonding member, and the elastic member form the first mechanical bond through the plurality of first mechanical structures; the first wire connecting member, the first bonding member, and the elastic member form the first electrical bond through the plurality of first electrical contacts; and the elastic member is electrically connected to the first signal connecting line to combine together the first bonding structure and the second bonding structure.

In accordance with another embodiment of the present disclosure, a bonding structure for a wearable device is provided. The bonding structure for a wearable device includes a wire connecting member, a bonding member and a signal connecting line. The wire connecting member includes a plurality of connectors, each of which has a plurality of first mechanical contacts, and a plurality of slots. The bonding member includes a plurality of second mechanical contacts. The signal connecting line has a plurality of first wires, wherein the plurality of first wires are respectively electrically connected to the plurality of slots for electrical connection to the wire connecting member; and the plurality of first mechanical contacts respectively inserted into the plurality of second mechanical contacts for mechanical connection to the bonding member.

In accordance with a further embodiment of the present disclosure, a node device for forming a sensing point on a first signal connecting line of a wearable device is provided, wherein the first signal connecting line has a plurality of signal wires, and is used for being connected to a sensing module to form the sensing point, and the node device comprises a wearable device body, a plurality of first connectors and a plurality of first electrical contacts. The plurality of first connectors are disposed on the wearing device body. The plurality of first electrical contacts are respectively disposed on the plurality of first connectors, and electrically connected to the plurality of signal wires to form the node device.

The above embodiments and advantages of the present invention will become more readily apparent to those ordinarily skilled in the art after reviewing the following detailed descriptions and accompanying drawings:

DETAILED DESCRIPTION OF THE PREFERRED EMBODIMENTS

Please refer to all FIGS. of the present invention when reading the following detailed description, wherein all FIGS. of the present invention demonstrate different embodiments of the present invention by showing examples, and help the skilled person in the art to understand how to implement the present invention. The present examples provide sufficient embodiments to demonstrate the spirit of the present invention, each embodiment does not conflict with the others, and new embodiments can be implemented through an arbitrary combination thereof, i.e., the present invention is not restricted to the embodiments disclosed in the present specification.

Figure 1A:
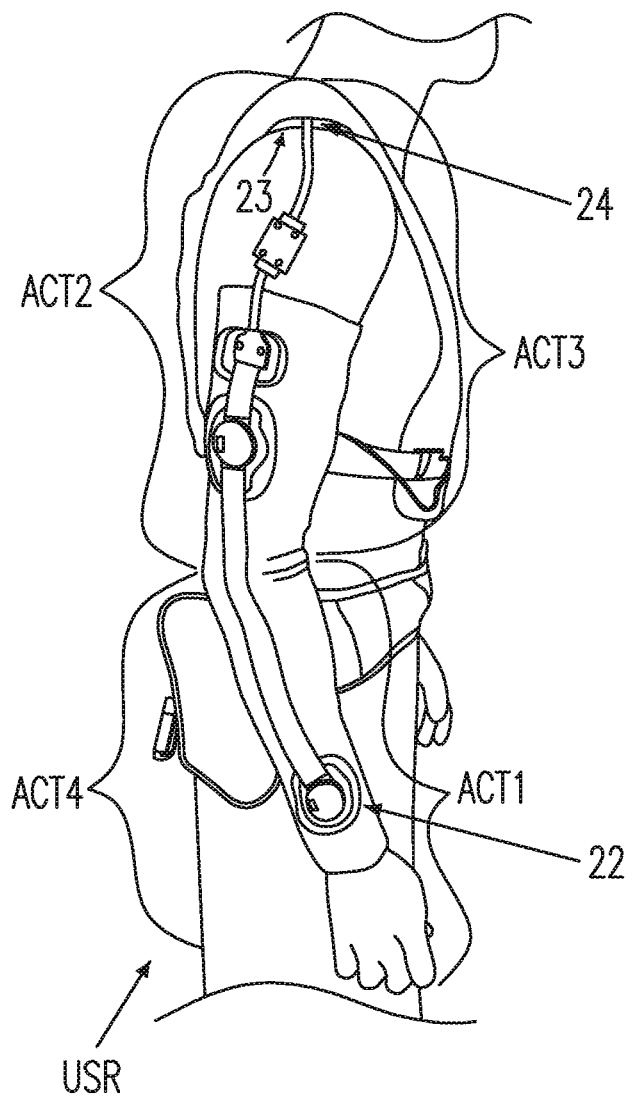
FIGS. 1A and 1B are schematic configuration diagrams showing a combined assembly of a wearable device on the limbs according to a preferred embodiment of the present disclosure.
Figure 1B:
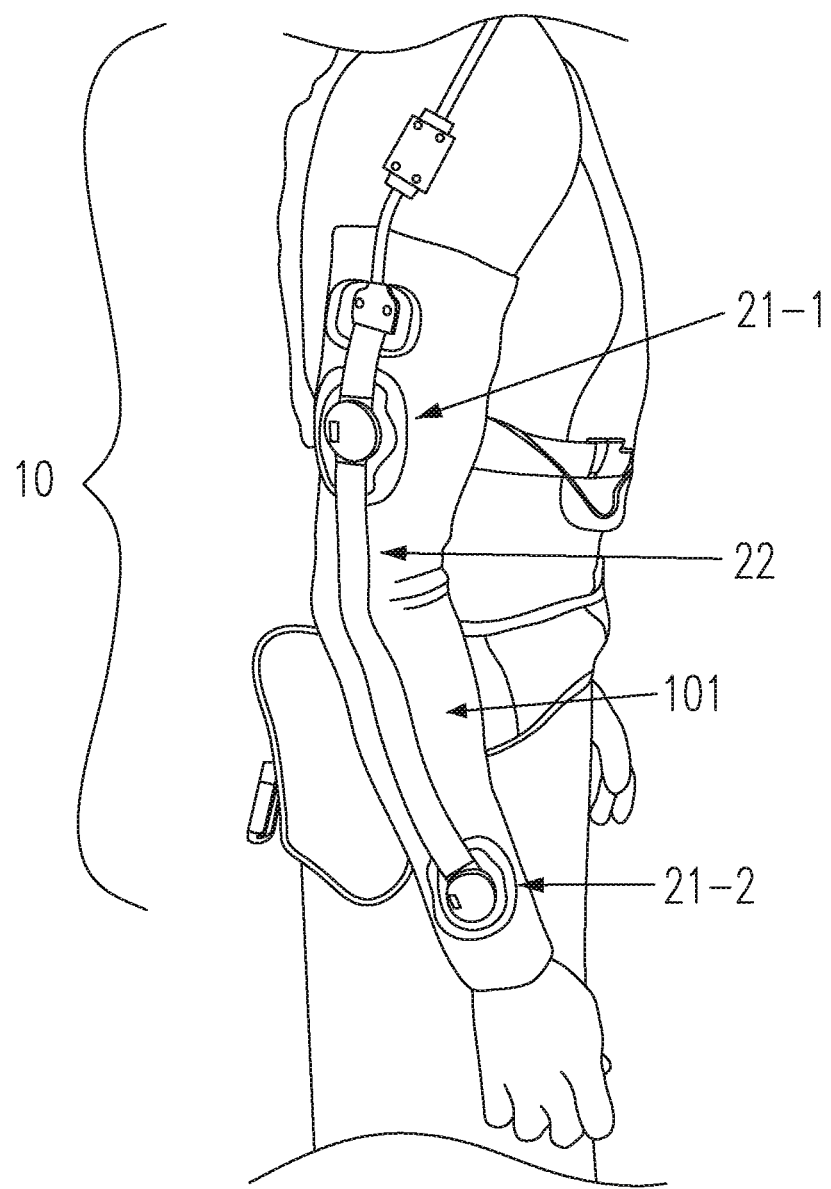
Figure 2:
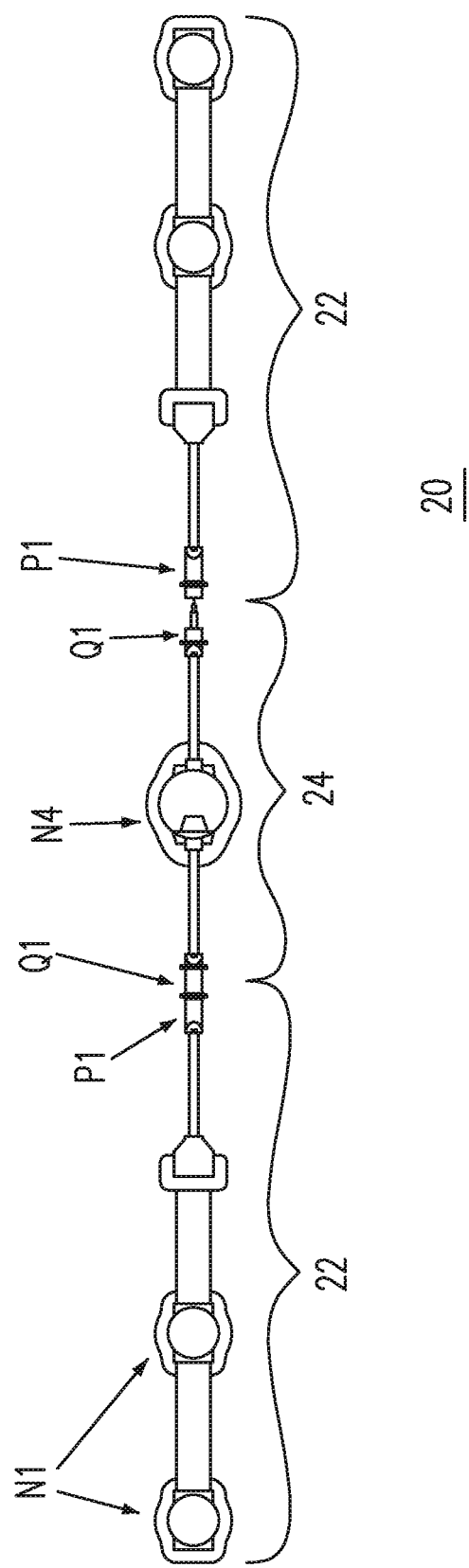
FIG. 2 is a schematic diagram showing bonding devices of a wearable device according to a preferred embodiment of the present disclosure.
Figure 3:
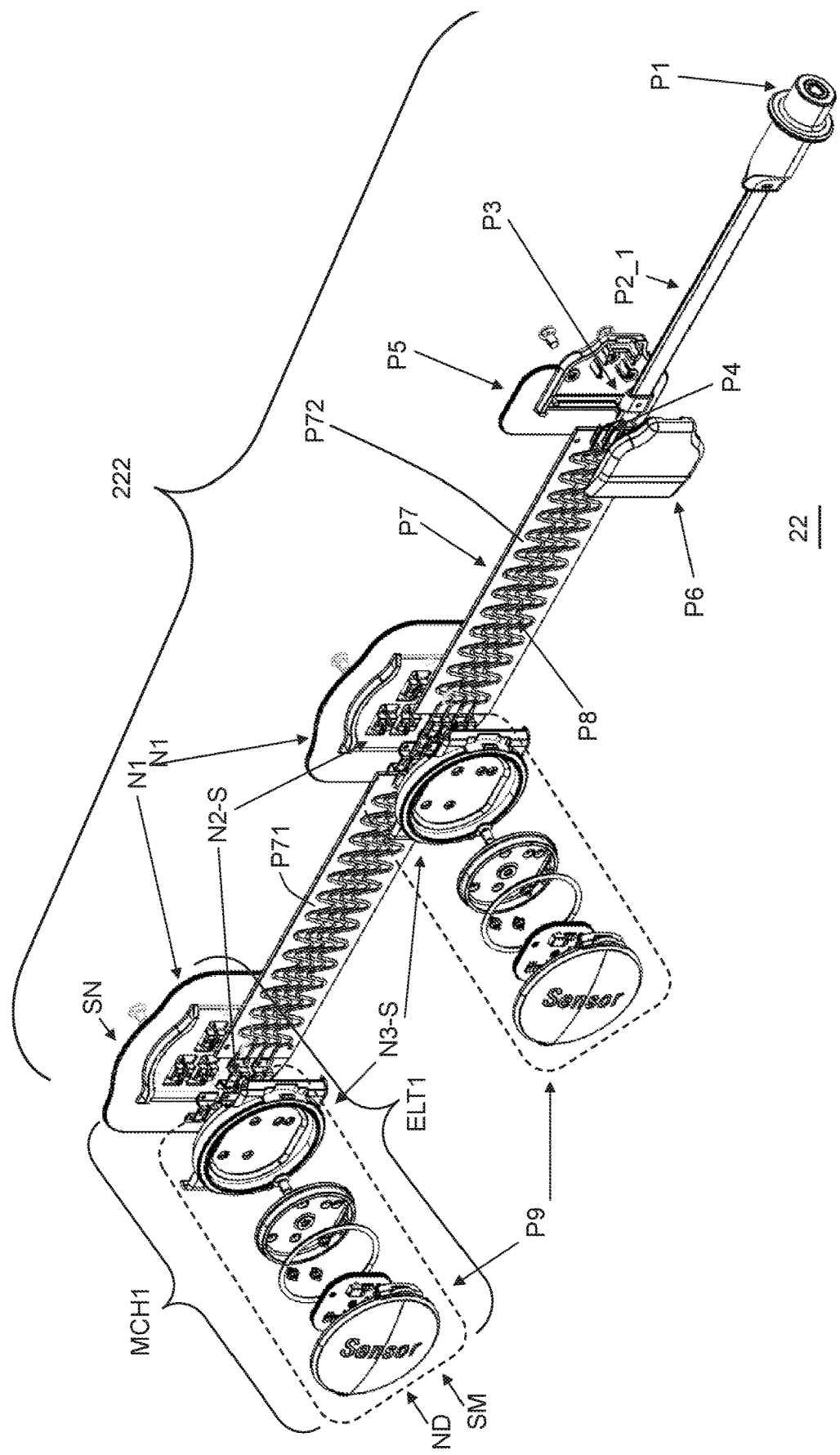
FIG. 3 is a schematic diagram showing a first bonding structure according to a preferred embodiment of the present disclosure.
Figure 4:
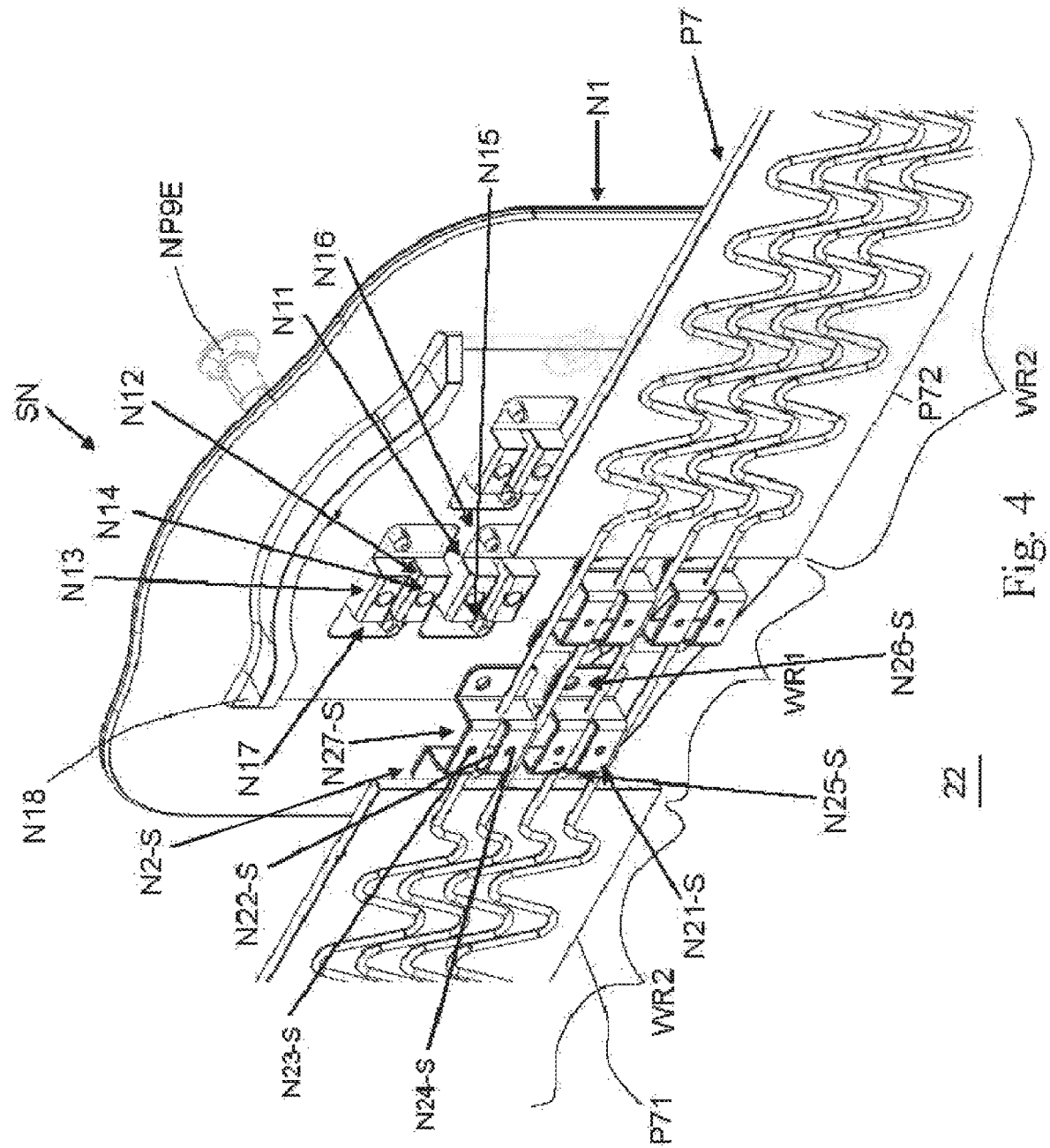
FIG. 4 is a schematic diagram showing an internal structure of the first bonding structure according to a preferred embodiment of the present disclosure.

Please refer to FIGS. 1A and 1B, which are schematic configuration diagrams showing a bonding device 20 of a wearable device 10 on the limbs according to a preferred embodiment of the present disclosure. Please refer to FIG. 2, which is a schematic diagram showing bonding structures 22 and 24 of a bonding device 20 according to a preferred embodiment of the present disclosure. Please refer to FIG. 3, which is a schematic diagram showing a first bonding structure 22 according to a preferred embodiment of the present disclosure. Please refer to FIG. 4, which is a schematic diagram showing an internal structure of the first bonding structure 22 according to a preferred embodiment of the present disclosure. Please refer to FIGS. 1, 2, 3 and 4 for the following descriptions. The bonding structure 22, 24 for a wearable device includes a first bonding structure 22 and a second bonding structure 24 (as shown in FIG. 2). The first bonding structure 22 has corresponding plural first mechanical structures (for example, N21-S, N11, N25-S, N26-S, N15 and N16 as shown in FIG. 4) and corresponding plural first electrical contacts (for example, N23-S, N24-S, N13 and N14 as shown in FIG. 4) to form a first mechanical bond MCH1 and a first electrical bond ELT1 (as shown in FIG. 3). The first bonding structure 22 includes a first wire connecting member N2-S, a first bonding member N1 and an elastic member P7. The first wire connecting member N2-S, the first bonding member N1 and the elastic member P7 are configured to form the first mechanical bond MCH1 through corresponding plural first mechanical structures, for example, N21-S (hole), N11 (protrusion), N25-S (hole not shown), N26-S (hole), N15 (protrusion) and N16 (protrusion). The first wire connecting member N2-S, the first bonding member N1 and the elastic member P7 are configured to form the first electrical bond ELT1 through the plurality of first electrical contacts, for example, N23-S (protruding type conduction member), N24-S (protruding type conduct member), N13 and N14. Please refer to FIG. 5, which is a schematic diagram showing a second bonding structure 24 according to a preferred embodiment of the present invention. The second bonding structure 24 includes a first signal connecting line P2_2. The plurality of first wires P8 attached on the elastic member P7, as shown in FIG. 4 3, are electrically connected to the plurality of second wires P4 of the first signal connecting line P2_1 to combine the first bonding structure 22 with the second bonding structure 24.

As shown in FIGS. 1A and 1B, the first bonding structure 22 and the second bonding structure 24 are attached to the fabric 101 by the attachment members 21 (21_1 and 21_2) shown in FIG. 1B, and 23 shown in FIG. 1A, for example, attached to the clothing of the user USR. The attachment members 21-1 and 21-2 of the first bonding structure 22 are respectively disposed on the upper arm and the lower arm of the user USR, in a non-joint position, so that sensors can detect motion status of the limbs of the user USR when the user USR exercises the limbs. In FIG. 1A, the attachment member 23 not shown, is located under the fabric on the shoulder.

In any one of the aforementioned embodiments of the present disclosure, the first wire connecting member N2-S includes a plurality of first connectors N21-S, each of which has a plurality of first mechanical contacts N25-S and N26-S and a plurality of first connecting slots N22-S. The first bonding member N1 includes a plurality of second connectors N1, each of which has a plurality of second mechanical contacts N15 and N16. For example, the plurality of first mechanical structures N21-S, N11, N25-S, N26-S, N15 and N16 include the plurality of first connectors N21-S, the plurality of second connectors N11, the plurality of first mechanical contacts N25-S and N26-S, and the plurality of second mechanical contacts N15 and N16. The elastic member P7 has a plurality of first wires P8. The plurality of first wires P8 are respectively inserted into (or embedded into or by means of soldering) the plurality of first connecting slots N22-S for electrically connecting the first wire connecting member N2-S. The plurality of first mechanical contacts N25-S and N26-S are respectively inserted into the plurality of second mechanical contacts N15 and N16, so that the plurality of first connectors N21-S are respectively inserted into the plurality of second connectors N11 for mechanically connecting the first bonding member N1. The arrangement of the plurality of first connectors N21-S may be interleaved for each other for adjacent connectors in a vertical direction.

In any one of the aforementioned embodiments of the present disclosure, the first bonding structure 22 is configured to be worn on an active portion (at least one of ACT1, ACT2, ACT3 and ACT4) of a user USR. The active portion (at least one of ACT1, ACT2, ACT3 and ACT4) includes at least one of limbs, head, neck, body and hips. The elastic member P7 is an elastic fabric member, and includes a plurality of elastic fabrics P71 and P72, as shown in FIG. 4, and a plurality of first wires P8 shown in FIG. 3, wherein the plurality of elastic fabrics P71 and P72 are attached thereon the plurality of first wires P8 respectively. Alternatively, the plurality of first wires P8 can be knitted on the plurality of elastic fabrics P71 and P72. The plurality of first wires P8 are evenly spaced, wavy, and thus flexible. Each of the plurality of first connectors N21-S is a conductor connector; and each of the plurality of second connectors N11 is an isolator. The plurality of second connectors N11 have a plurality of second connecting slots N12 respectively. The plurality of first wires P8 are respectively inserted into the plurality of first connecting slots N22-S for electrically connecting; and then the plurality of first connecting slots N22-S are arranged in the plurality of second slots N12 for mechanically connecting the first bonding member N1. The plurality of first mechanical contacts N25-S and N26-S include a plurality of via holes (for example, a left side hole N25-S and a right side hole N26-S); and the plurality of second mechanical contacts N15 and N16 include a plurality of protrusions (for example, a left protrusion N15 and a right protrusion N16) respectively inserted into the plurality of via holes for connecting with the plurality of first connectors N21-S mechanically. Each of the plurality of first connectors N21-S has a concave portion N27-S and a plurality of first electrical contacts N23-S, N24-S located at a bottom of the concave portion N27-S, each of the plurality of second connectors N1 has a protruding portion N17, an upper connector hole N13 and a lower connector hole N14 located at a top of the corresponding protruding portion N17. Each of the plurality of protruding portions N17 is inserted into the respective concave portion N27-S; and the plurality of first electrical contacts N23-S and N24-S are a pair of contacts respectively mechanically connected to the upper connector hole N13 and the lower connector hole N14, such that the plurality of first connectors N21-S and the plurality of second connectors N11 are respectively connected mechanically. In FIG. 4, the plurality of electrical contacts N23-S and N24-S are an upper hole N23-S and a lower hole N24-S of the first connector N21-S.

Figure 6:
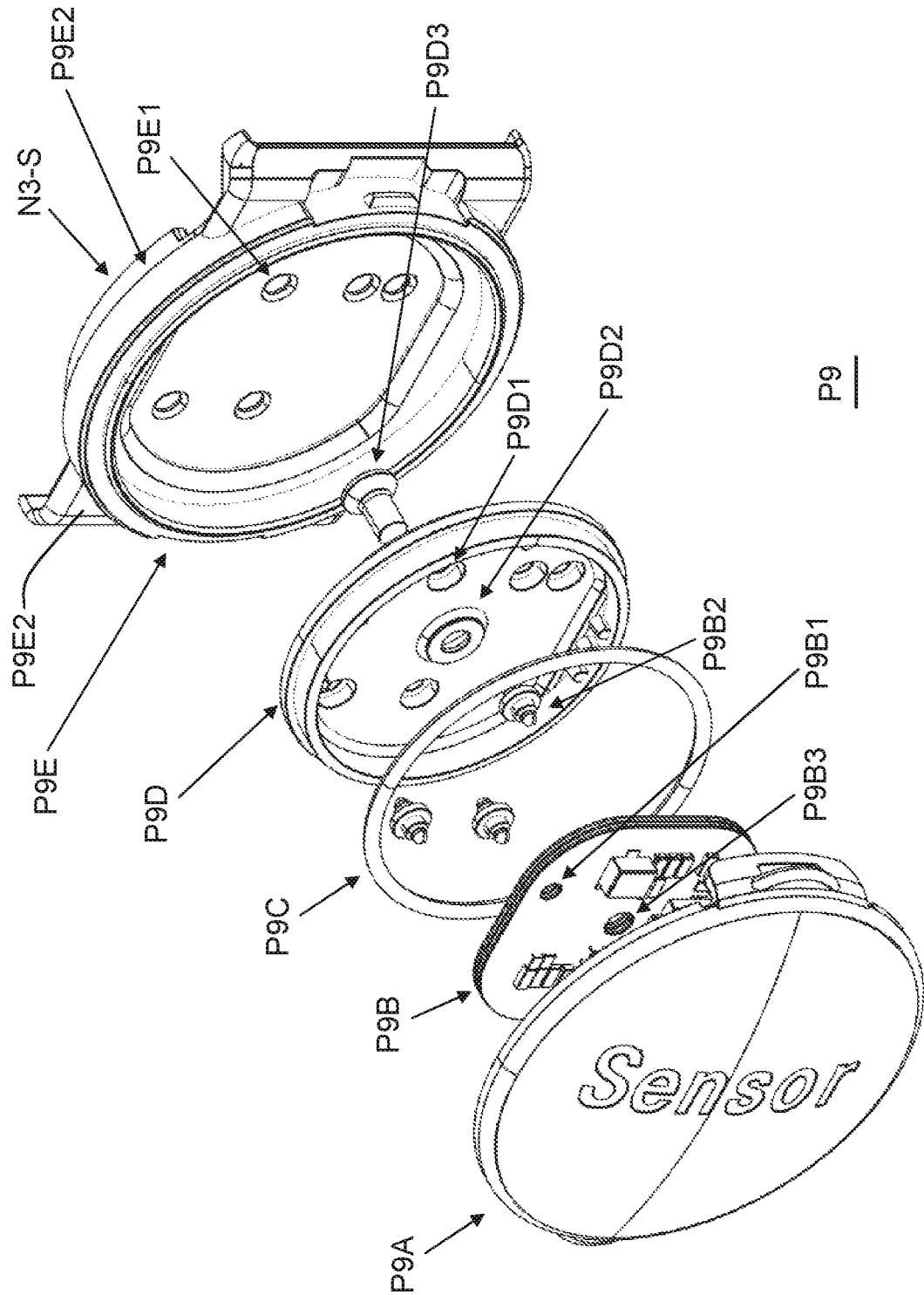
FIG. 6 is a schematic diagram showing a rigid unit according to the preferred embodiment of the present invention.

Please refer to FIG. 6, which is a schematic diagram showing a rigid unit P9 according to the preferred embodiment of the present invention. Please refer to FIG. 7, which is a schematic diagram showing electrical holes for identifying positions of a rigid unit P9 according to the preferred embodiment of the present invention. Please refer to FIGS. 6 and 7 for the following descriptions. For example, the rigid unit P9 is a motion sensing module, which includes a module connector N3-S (i.e., a module connector P9E of the rigid unit P9), a PCB (Print Circuit Board) connector P9D, an engaging ring P9C, a PCB P9B and a protection cover P9A.

Figure 7:
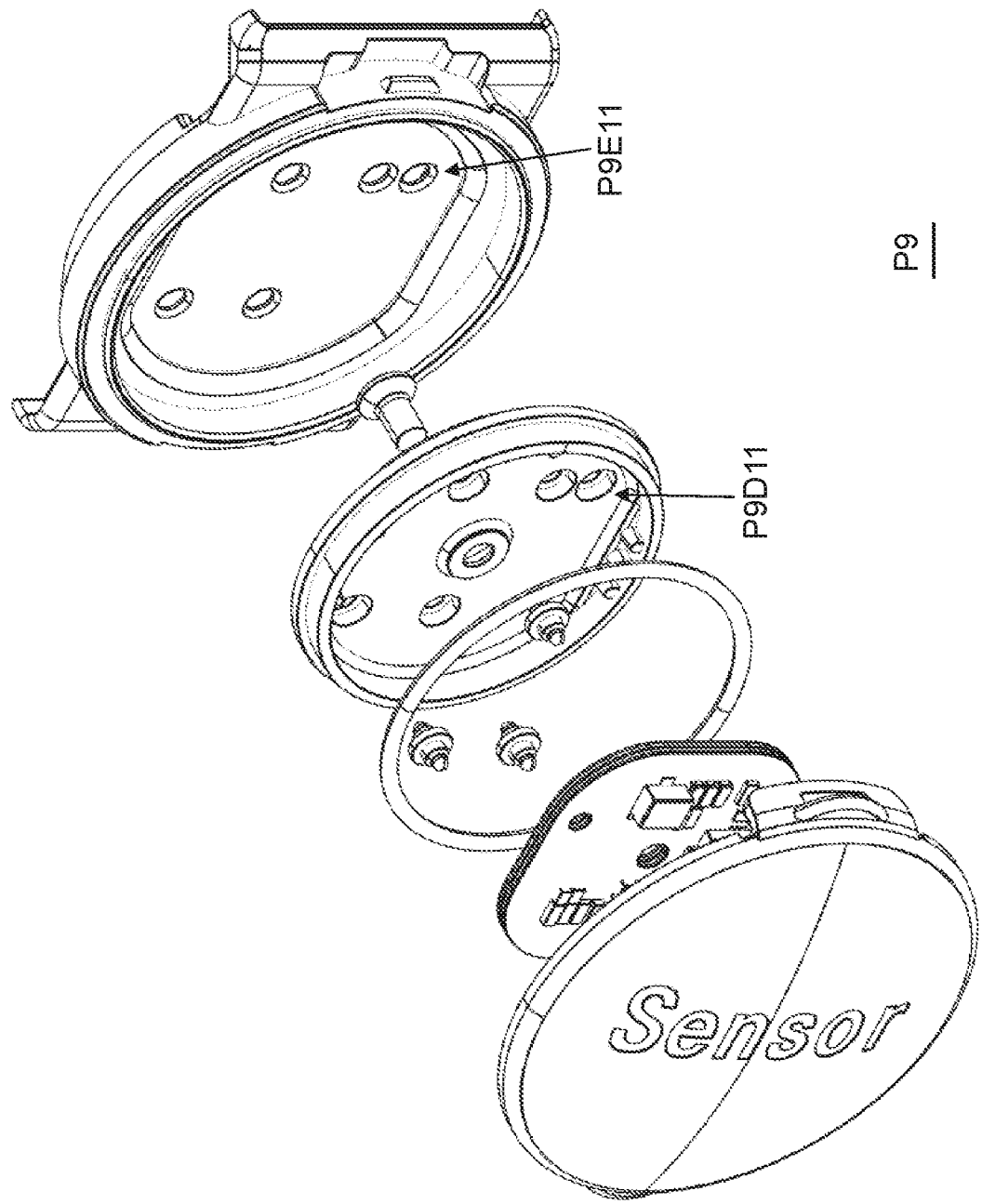
FIG. 7 is a schematic diagram showing electrical holes for identifying positions of the rigid unit according to a preferred embodiment of the present invention.

Please refer to FIGS. 4, 6 and 7. In any one of the aforementioned embodiments, the first wire connecting member N2-S includes the plurality of first electrical contacts N23-S and N24-S. The first bonding structure 22 further includes a rigid unit P9 having a plurality of second electrical contacts P9E1, P9D1, P9B2, P9B1, P9E11 and P9D11 (as shown in FIGS. 6 and 7); and the plurality of second electrical contacts P9E1, P9D1, P9B2 and P9B1 are electrically connected to the plurality of first electrical contacts N23-S and N24-S to electrically connect the rigid unit P9 to the first wire connecting member N2-S (as shown in FIGS. 4, 6 and 7). At least one of the plurality of second electrical contacts P9E1, P9D1, P9B2, P9B1, P9E11 and P9D11 (for example, P9E11 and P9D11) is used to form a conduction or a disconnection, wherein the conduction or the disconnection is used to determine a wearing position of the rigid unit P9.

In FIG. 6, the PCB P9B is fixed to the PCB base P9D through the PCB base positioning hole P9B3, the PCB base positioning hole P9D2, the PCB fixing member P9D3, and the electrical contacts P9B1 and P9D1; and the engaging ring P9C is sleeved on the PCB base P9D, and is then plugged into the module connection base N3-S, so that the PCB base P9D is fixed in the module connection base N3-S, and then the cover P9A covers the module connection base N3-S. Please refer to FIGS. 4, 6 and 7. In any one of the aforementioned embodiments, the module connection base N3-S has a curved protrusion structure P9E2, and the first bonding member N1 also has a curved dike structure N18, which is used to fix the module connection base N3-S to the first bonding member N1. Each of the plurality of second connectors N11 further includes a plurality of holes N13 and N14, wherein the plurality of first electrical contacts N23-S and N24-S are respectively coupled to the plurality of holes N13 and N14 and the plurality of second electrical contacts P9E1, P9D1, P9B2, P9B1, P9E11 and P9D11, such that the rigid unit P9 is fixed to the first bonding member N1. The stabilization unit NP9E passes through the first bonding member N1 and is locked into an internal screw hole (located on the back of the module connection base N3-S, not shown) of the module connection base N3-S, so that the rigid unit P9 is directly connected with the first bonding member N1 to mechanically increase the stability of the rigid unit P9 and avoid loosening.

In FIG. 3, the first bonding structure 22 further includes a signal line fixing component P3 and a second signal connecting line P2_1. The second signal connecting line P2_1 includes a plurality of second wires P4 and a signal connecting hole P1, wherein the plurality of first wires P8 are electrically connected to the plurality of second wires P4 respectively at the signal line fixing component P3. The signal line fixing element P3 includes a protection cover P6 and a protection base P5 for fixing and packaging the plurality of second wires P4 to ensure the transmission of electrical signals. The first bonding structure 22 is combined with the second bonding structure 24 to form the bonding device 20, wherein the second bonding structure 24 includes a signal connector Q1 (as shown in FIG. 2) for electrically connecting the signal connecting hole P1.

Figure 8:
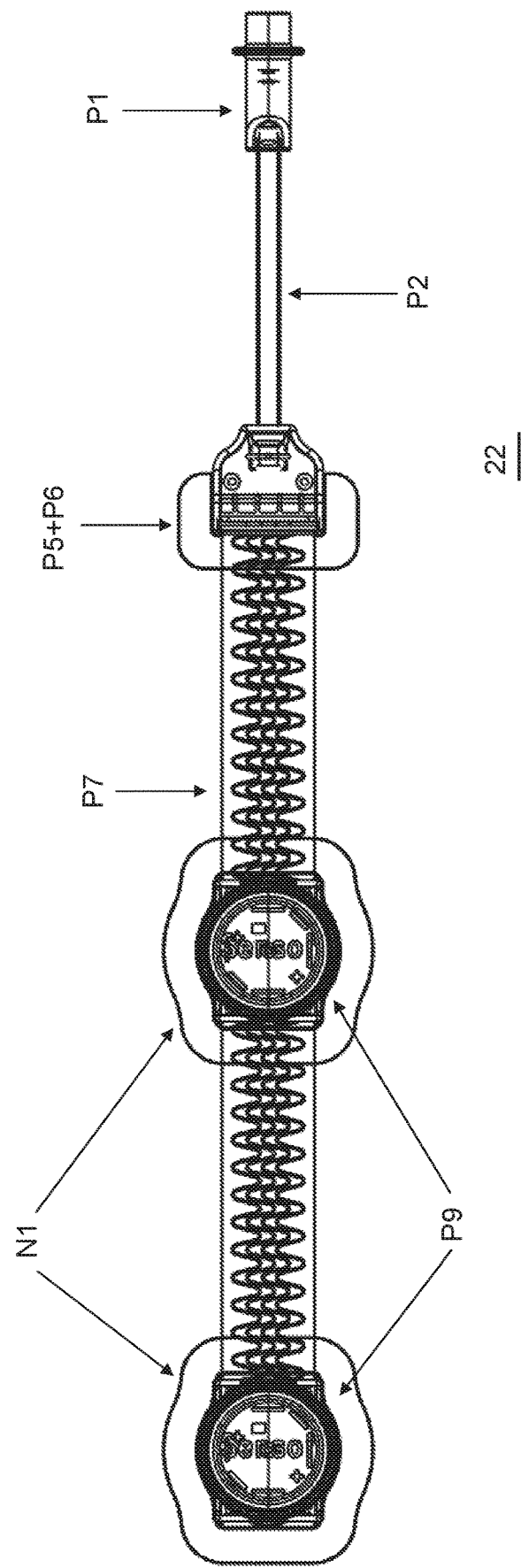
FIG. 8 is a schematic diagram showing a first bonding structure according to a preferred embodiment of the present invention.

Please refer to FIG. 8, which is a schematic diagram showing a first bonding structure 22 according to a preferred embodiment of the present invention. It can be seen in FIG. 8 that the first bonding structure 22 includes two rigid units P9 (such as a motion sensing module), each of the first bonding members N1 and each of the first wire connecting members N2-S are used to connect each of the rigid unit P9 to the flexible member P7 having a flexible plurality of first wires P8 by the mechanical bond MCH1 and the electrical bond LET1 (as shown in FIGS. 3, 4 and 8). The protection cover P6 and the protection base P5 are used to fix the plurality of flexible wires P8 and the signal connecting line P2_1. The signal sensed by the motion sensing module can be transmitted to the data collection center through the signal connecting line P2_1, and then transmitted to the back-end computing center by the data collection center for analysis.

Figure 9:
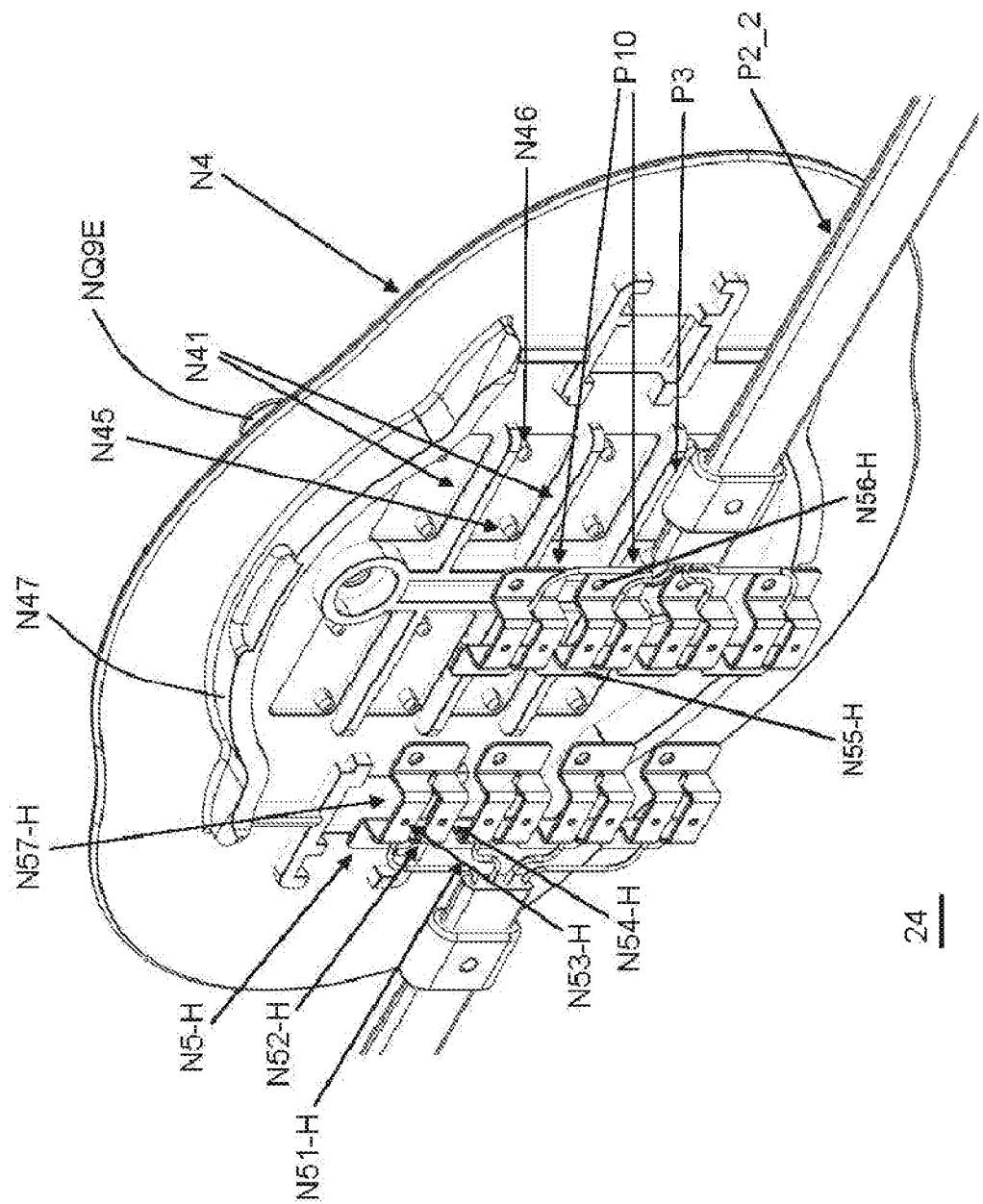
FIG. 9 is a schematic diagram showing an internal structure of a second bonding structure according to a preferred embodiment of the present invention.

Please refer to FIG. 9, which is a schematic diagram showing an internal structure of a second bonding structure 24 according to a preferred embodiment of the present invention. Please refer to FIGS. 5 and 9. The second bonding structure 24 further includes a second wire connecting member N5-H having a plurality of third connectors N51-H, each of which has a third connecting slot N52-H and a plurality of third mechanical contacts N55-H and N56-H, for example, a left side hole N55-H (hole not shown) and a right side hole N56-H of the second wire connecting member N5-H. The second bonding structure 24 further includes a second bonding member N4 including a plurality of fourth mechanical contacts N45 and N46, each of the position of which is arranged according to each of the third mechanical contacts N55-H and N56-H correspondingly, for example, a left positioning protrusion N45 and a right positioning protrusion N46 on the second bonding member N4. The signal connecting line P2_2 has a plurality of second wires P10. The plurality of third connectors N51-H have a plurality of third connecting slots N52-H respectively. The plurality of second wires P10 are inserted into (or soldered to) the plurality of third connecting slots N52-H respectively, for electrically connecting to the second wire connecting member N5-H. The plurality of third mechanical contacts N55-H and N56-H are inserted by the plurality of fourth mechanical contacts N45 and N46 correspondingly, for connecting with the second bonding member N4 mechanically. The second bonding structure 24 is detachably fitted to a relatively stable portion of a user USR, for example, the stable portion includes at least one of a shoulder, a chest, a back and a waist. The second bonding member N4 further includes a plurality of positioning protrusions N41. The plurality of third connectors N51-H are configured to mechanically connect to the second bonding member N4 according to the plurality of positioning protrusions N41; for example, each of the plurality of positioning protrusions N41 is a positioning board. Each of the plurality of third connectors N51-H is a conductor connector, and the plurality of positioning protrusions N41 are respectively a plurality of insulator protrusions. The plurality of third mechanical contacts N55-H and N56-H include a plurality of via holes; and the plurality of fourth mechanical contacts N45 and N46 include a plurality of fixing protrusions. The plurality of fixing protrusions respectively penetrate the plurality of via holes to mechanically connect to the plurality of third connectors N51-H. Each of the third connectors N51-H further has a recess N57-H and a plurality of first electrical contacts N53-H and N54-H located on the recess N57-H, for example, an upper hole N53-H and a lower hole N54-H of each of the third connector N51-H.

Figure 10:
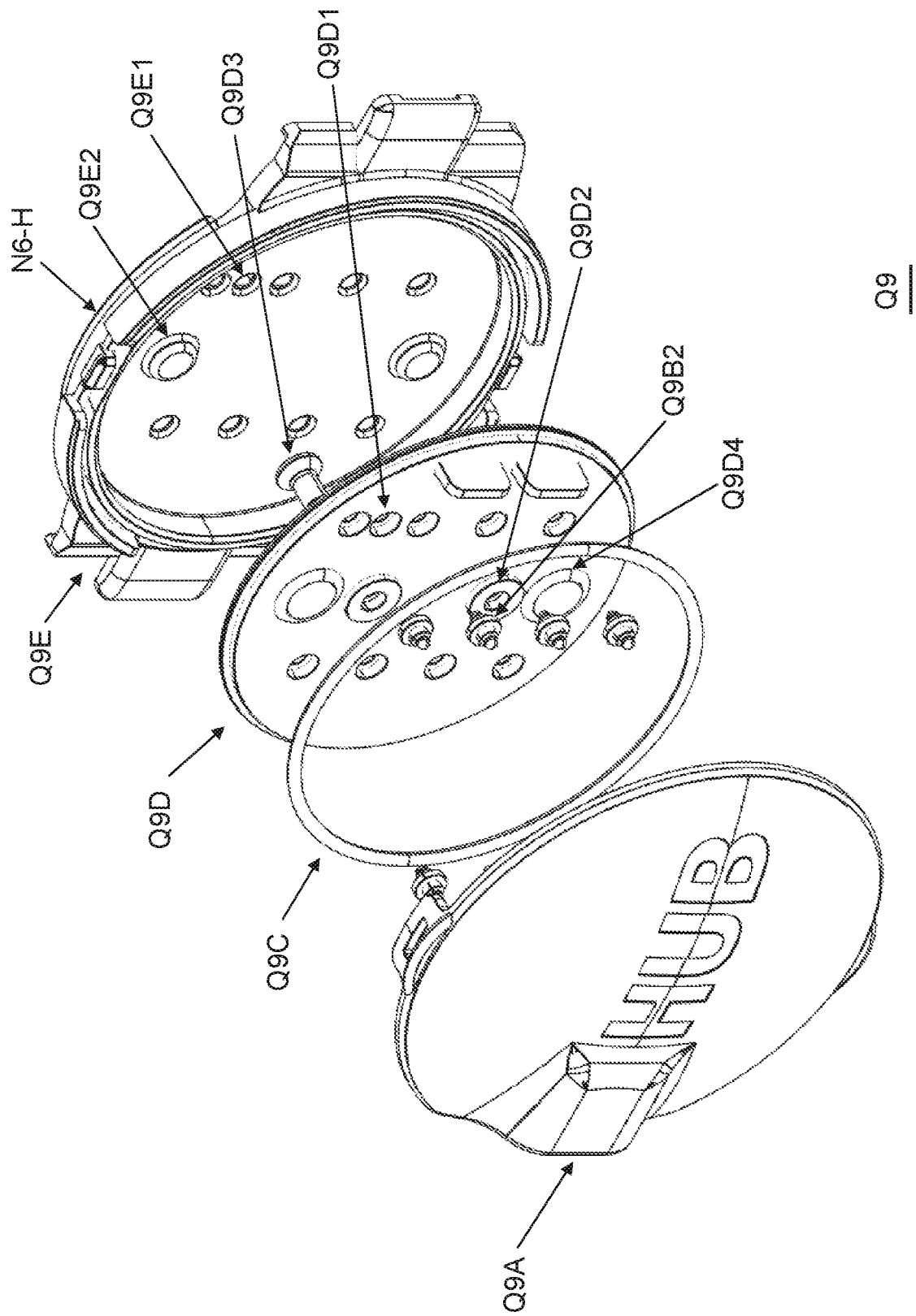
FIG. 10 is a schematic diagram showing another rigid unit according to the preferred embodiment of the present invention.

Please refer to FIG. 10, which is a schematic diagram showing another rigid unit Q9 according to the preferred embodiment of the present invention. Please refer to FIG. 11, which is a schematic diagram showing electrical holes for identifying positions of another rigid unit Q9 according to a preferred embodiment of the present invention. Please refer to FIGS. 10 and 11. For example, the rigid unit Q9 is a signal processing module, which includes a module connector N6-H, a PCB base Q9D, an engaging ring Q9C, a PCB Q9B (not shown) and a protection cover Q9A.

Figure 11:
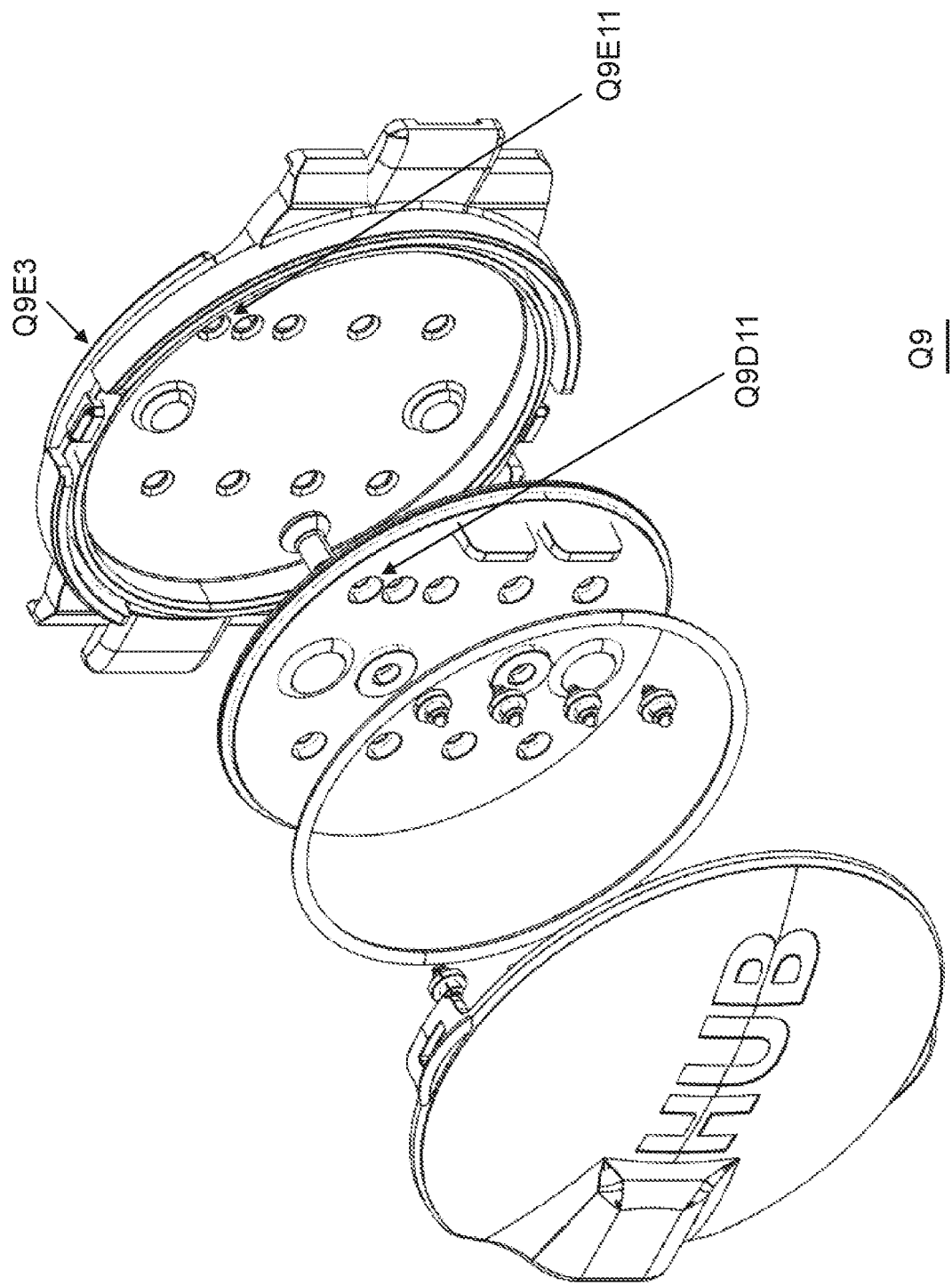
FIG. 11 is a schematic diagram showing electrical holes for identifying positions of another rigid unit according to a preferred embodiment of the present invention.

Please refer to FIGS. 9, 10 and 11. In any one of the aforementioned embodiments, the second wire connecting member N5-H includes the plurality of first electrical contacts N53-H and N54-H. The first second bonding structure 24 further includes a rigid unit Q9 having a plurality of fourth electrical contacts Q9E1, Q9D1, Q9B2, Q9B1 (not shown), Q9E11 and P9D11 (as shown in FIGS. 10 and 11); and the plurality of fourth electrical contacts Q9E1, Q9D1, Q9B2 and Q9B1 are electrically connected to the plurality of third electrical contacts N53-H and N54-H to electrically connect the rigid unit Q9 to the second wire connecting member N5-H (as shown in FIGS. 9, 10 and 11). At least one of the plurality of fourth electrical contacts Q9E1, Q9D1, Q9B2, Q9B1, Q9E11 and Q9D11 (for example, QC11, Q9E11 and Q9D11) is used to form a conduction or a disconnection, wherein the conduction or the disconnection is used to determine a wearing position of the rigid unit Q9.

In FIG. 10, the PCB Q9B (not shown) is fixed to the PCB base Q9D through the PCB base positioning hole Q9B3 (not shown), the PCB base positioning hole Q9D2, the PCB fixing member Q9D3, and the electrical contacts Q9B1 (not shown) and Q9D1; and the engaging ring Q9C is sleeved on the PCB base Q9D, and is then plugged into the module connection base N6-H (i.e., Q9E), so that the PCB base Q9D is fixed in the module connection base N6-H, and then the cover Q9A covers the module connection base N6-H (i.e., Q9E). Please refer to FIGS. 5, 10 and 11. In any one of the aforementioned embodiments, the module connection base Q9E has a curved protrusion structure Q9E3, and the second bonding member N4 also has a curved dike structure N47, which is used to fix the module connection base Q9E to the second bonding member N4. The plurality of third electrical contacts N53-H and N54-H are respectively coupled to the plurality of fourth electrical contacts Q9E1, Q9D1, Q9B2, Q9B1, Q9E11 and Q9D11, such that the rigid unit Q9 is fixed to the second bonding member N4, and the rigid unit Q9 is electrically connected with the signal connecting line P2_2. The stabilization unit NQ9E (not shown) passes through the second bonding member N4 and is locked into an internal screw hole (located on the back of the module connection base Q9E, not shown) of the module connection base Q9E, so that the rigid unit Q9 is directly connected with the second bonding member N4 to mechanically increase the stability of the rigid unit Q9 and avoid loosening. The second bonding structure 24 is combined with the first bonding structure 22 to form the bonding device 20. The signal connecting line P2_2 further includes a signal connector Q1; and the first bonding structure 22 includes a signal connecting hole P1 for being electrically connected to the signal connector Q1.

Figure 5:
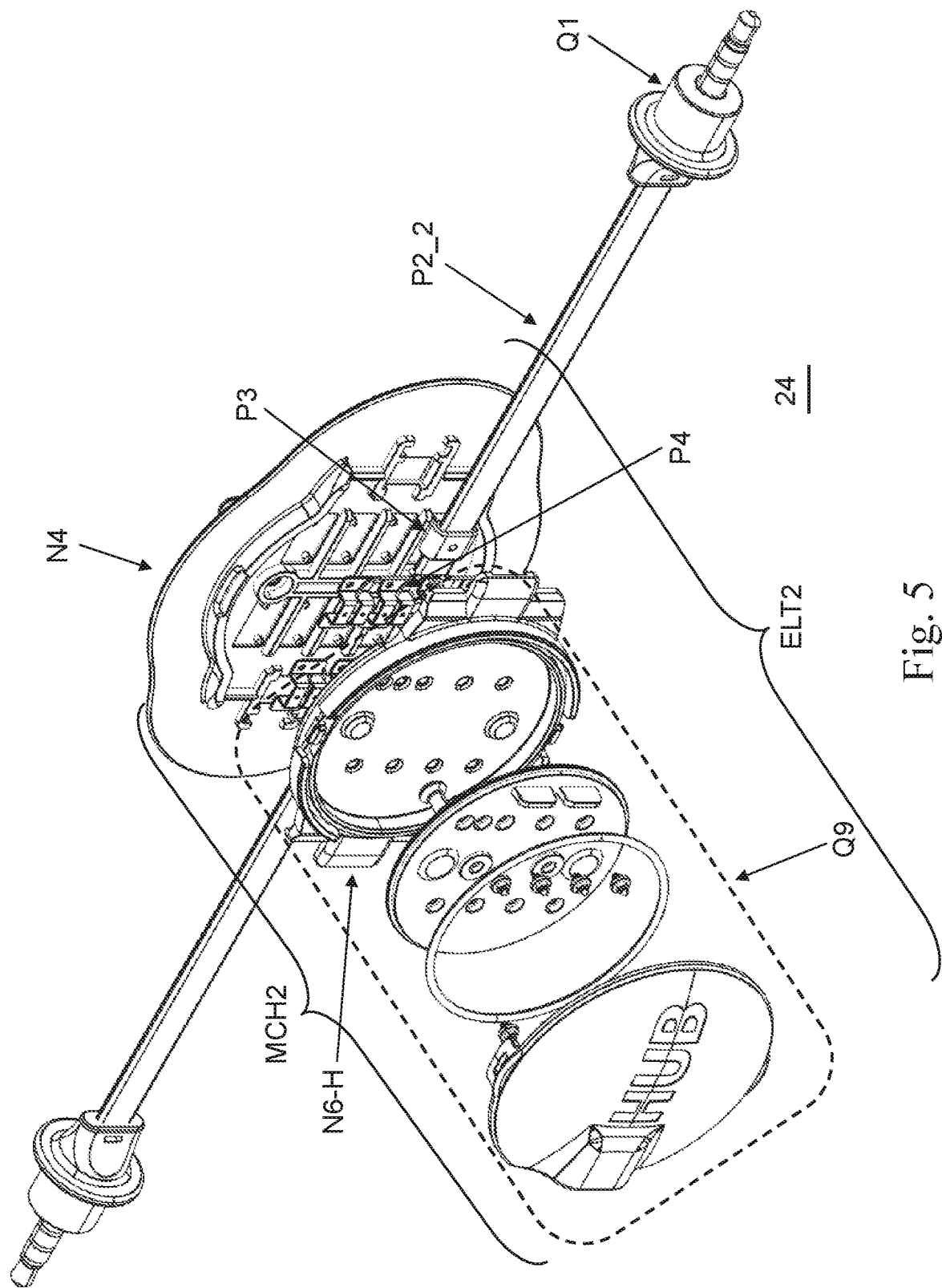
FIG. 5 is a schematic diagram showing a second bonding structure according to a preferred embodiment of the present invention.

In FIG. 5, the second bonding structure 24 further includes a signal line fixing component P3 and another signal connecting line P2_2. The bonding structure 24 includes a plurality of second wires P10 and the signal connector Q1, wherein the plurality of second wires P10 are electrically connected with the plurality of second wires P4 respectively at the signal line fixing component P3.

Figure 12:
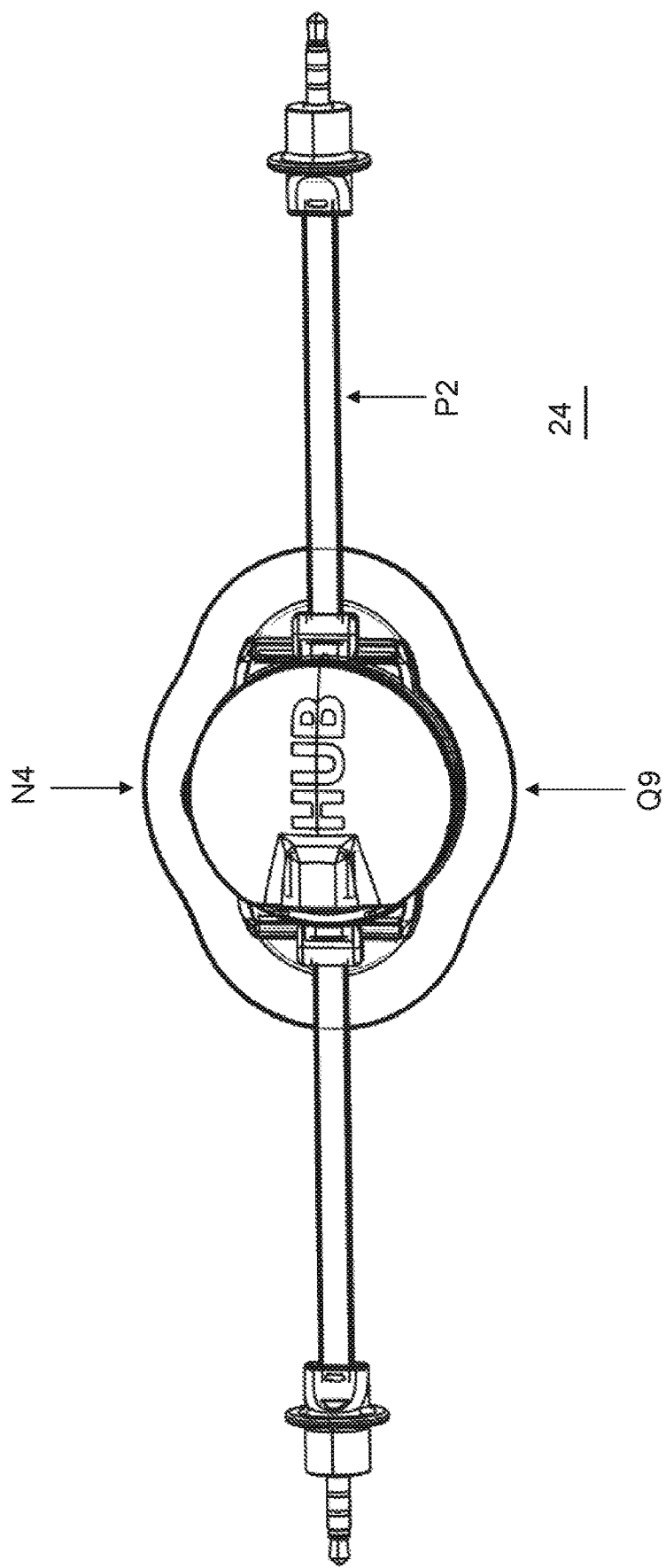
FIG. 12 is a schematic diagram showing a second bonding structure according to another preferred embodiment of the present invention.

Please refer to FIG. 12, which is a schematic diagram showing a second bonding structure 24 according to another preferred embodiment of the present invention. It can be seen in FIGS. 5, 9 and 12 that the second bonding structure 24 includes a rigid unit Q9, such as a signal processing module. The second bonding member N4 and the second wire connecting member N5-H are used to connect and fix the rigid unit Q9 to two signal connecting lines P2_2 by a mechanical bond MCH2 and an electrical bond ELT2. The signal processing module can receive a sensing signal from the sensing module, for example, an (angular) acceleration signal, a (angular) velocity signal and so on, and can transmit it to the data collecting center, and then the data collecting center transmits it to the back-end computer center for analysis. The rigid unit Q9 or P9 may be fixed on an attachment member 21, for example, fabrics or leathers, and then the attachment member 21 is attached on clothes worn by the user USR. The attachment method can be adhesive, sewing for fixedly attaching, or by using a Velcro, zippers, buttons or other detachable fasteners. They are detachably fixed on the attachment member 21 as shown in FIGS. 1A and 1B, and then the attachment member 21 is arranged on the fabric 101 worn on a limb. The rigid unit Q9 or P9 can be detached, so that the fabric 101 can be washed by water like a conventional fabric. In addition, the rigid unit Q9 or P9 can be increased or decreased to be worn on the limbs according to application needs, wherein the rigid unit Q9 can be the signal processing/transmitting module, the device, or the rigid unit P9, i.e., the motion sensing module or device.

Please return to FIGS. 3 and 4, which show another preferred embodiment of the invention for a bonding structure 22 for a wearable device. The bonding structure 22 includes a wire connecting member N2-S, a bonding member N1 and an elastic member P7. In any one of aforementioned embodiments, the wire connecting member N2-S includes a plurality of first connectors N21-S, each of which has a plurality of first mechanical contacts N25-S (holes not shown) and N26-S, and the plurality of first connectors have a plurality of first connecting slots N22-S respectively. The bonding member N1 includes a plurality of second connectors N11, each of which has a plurality of second mechanical contacts N15 (protrusion) and N16 (protrusion). The elastic member P7 has a plurality of first wires P8, wherein the plurality of first wire P8 are correspondingly inserted into (or soldered to) the plurality of first connecting slots N22-S, and thereby are electrically connected to the wire connecting member N2-S. The plurality of first mechanical contacts N25-S (holes not shown) and N26-S (holes) are correspondingly embedded into the plurality of second mechanical contacts N15 (protrusion) and N16 (protrusion), and thereby the plurality of first connectors N21-S are correspondingly embedded into the plurality of second connectors N11 so as to connect with the bonding member N1 mechanically.

Please return to FIGS. 5 and 9, which show another preferred embodiment of the invention for a bonding structure 24 for a wearable device. The bonding structure 24 includes a wire connecting member N5-H, a bonding member N4 and a signal connecting line P2_2. In any one of the aforementioned embodiments, the wire connecting member N5-H includes a plurality of connectors N51-H, each of which has a plurality of first mechanical contacts N55-H (holes not shown) and N56-H (hole), and the plurality of connectors N51-H have a plurality of connecting slots N52-H respectively. The bonding member N4 includes a plurality of second mechanical contacts N45 (protrusion) and N46 (protrusion). The signal connecting line P2_2 has a plurality of first wires P10, electrically connecting to the plurality of connecting slots N52-H correspondingly, so as to electrically connect with the wire connecting member N5-H. The plurality of first mechanical contacts N55-H and N56-H are inserted into the plurality of second mechanical contacts N45 and N46 correspondingly, so as to mechanically connect with the bonding member N4.

Please refer to FIGS. 3 and 4 again, which show a node device ND according to a preferred embodiment of the present invention. In any one of the aforementioned embodiments, the node device ND is configured to form a sensing point SN on a signal connecting line P2_1 of a wearable device. The signal connecting line P2_1 has a plurality of signal wires P8, and is used for being connected to a sensing module SM to form the sensing point SN; and the node device SM includes a wearable device body 222, a plurality of first connectors N21-S and a plurality of first electrical contacts N23-S and N24-S. The plurality of first connectors N21-S are disposed on the wearing device body 222. The plurality of first electrical contacts N23-S and N24-S and a plurality of connecting slots N22-S are respectively disposed on the plurality of first connectors N21-S, and electrically connected to the plurality of signal wires P8 to form the node device ND.

In FIG. 4, a signal connecting wire WR is additionally shown according to a preferred embodiment of the present invention. The signal wires WR for the wearable device includes a line base material P7 and a plurality of signal lines P8. The plurality of signal lines P8 are arranged on the line base material P7, wherein each of the plurality of the signal lines P8 has a first part WR1 and a second part WR2. Each first part WR1 forms a sensing node SN for connecting a sensing module SM for forming the sensing node SN, wherein each first part WR1 is a straight line.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A bonding device (20) for a wearable device (10), comprising:
   a first bonding structure (22) having a plurality of first mechanical structures (MCH1) configured to form a first mechanical bond and a plurality of first electrical contacts (N23-S, N24-S, N13, N14) configured to form a first electrical bond (ELT1), and including:
      a first wire connecting member (N2-S);
      a first bonding member (N1); and
      a plurality of first wires (WR) disposed on an elastic member (P7); and
   a second bonding structure (24) including a first signal connecting line (P2_2), wherein:
   the first wire connecting member (N2-S), a second bonding member (N4), and a rigid unit (Q9) form a second mechanical bond (MECH2);
   the first wire connecting member (N2-S), the first bonding member (N1), and the signal connecting wire (WR) form the first electrical bond (ELT1) through the plurality of first electrical contacts (N23-S, N24-S, N13, N14); and
   the elastic member (P7) is electrically connected to the first signal connecting line (P2_2) to combine together the first bonding structure (22) and the second bonding structure (24).

2. The bonding device as claimed in claim 1, wherein:
   the first wire connecting member includes a plurality of first connectors, each of which has a plurality of first mechanical contacts and a plurality of first connecting slots;
   the first bonding member includes a plurality of second connectors, each of which has a plurality of second mechanical contacts; and
   the plurality of first mechanical structures include the plurality of first connectors, the plurality of second connectors, the plurality of first mechanical contacts and the plurality of second mechanical contacts.

3. The bonding device as claimed in claim 2, wherein:
   the elastic member has the plurality of first wires;
   each of the plurality of first connectors is a conductor connector, and each of the plurality of second connectors is an isolator;
   the plurality of second connectors have a plurality of second connecting slots respectively; and
   the plurality of first wires are respectively inserted into the plurality of second connectors for mechanically connecting the first bonding member.

4. The bonding device as claimed in claim 2, wherein:
   the plurality of first mechanical contacts include a plurality of via holes, and the plurality of second mechanical contacts include a plurality of protrusions respectively inserted into the plurality of via holes for connecting with the plurality of first connectors;
   each of the plurality of first connectors has a concave portion and the plurality of first electrical contacts located at a bottom of the concave portion, each of the plurality of second connectors has a protruding portion, an upper connector hole and a lower connector hole located at a top of the corresponding protruding portion;
   each of the plurality of protruding portions is inserted into the respective concave portion, and the plurality of first electrical contacts are a pair of contacts respectively mechanically connected to the upper connector hole and the lower connector hole, such that the plurality of first connectors and the plurality of second connectors are respectively connected mechanically.

5. The bonding device as claimed in claim 2, wherein:
   the first wire connecting member includes the plurality of first electrical contacts;
   the first bonding structure further comprises a rigid unit having a plurality of second electrical contacts electrically connected to the plurality of first electrical contacts to electrically connect the rigid unit to the first wire connecting member;
   at least one of the plurality of second electrical contacts is used to form a conduction or a disconnection, wherein the conduction or the disconnection is used to determine a wearing position of the rigid unit;
   the rigid unit is a motion sensing module; and
   each of the plurality of second connectors further includes a plurality of holes, wherein the plurality of first electrical contacts are respectively coupled to the plurality of holes and the plurality of second electrical contacts such that the rigid unit is fixed to the first bonding member.

6. The bonding device as claimed in claim 2, wherein:
   the elastic member has a plurality of first wires;
   the plurality of first wires are respectively inserted into the plurality of first connecting slots for electrically connecting the first wire connecting member; and
   the plurality of first mechanical contacts are respectively inserted into the plurality of second mechanical contacts such that the plurality of first connectors are respectively inserted into the plurality of second connectors for mechanically connecting the first bonding member.

7. The bonding device as claimed in claim 1, wherein:
   the first bonding structure is configured to be worn on an active portion of a user;
   the active portion includes at least one of limbs, head, neck, body and hips;
   the elastic member is an elastic fabric member, and includes a plurality of elastic fabrics and a plurality of first wires, wherein the plurality of first wires respectively are attached on the plurality of elastic fabrics; and
   the plurality of first wires are evenly spaced, wavy, and flexible.

8. The bonding device as claimed in claim 1, wherein:
   the elastic member has a plurality of first wires;
   the first bonding structure further comprises:
      a signal line fixing component; and
      a second signal connecting line including a plurality of second wires and a signal connecting hole, wherein the plurality of first wires are electrically connected to the plurality of second wires respectively at the signal line fixing component; and
   the first bonding structure is combined with the second bonding structure to form the bonding device, wherein the second bonding structure includes a signal connector for electrically connecting the signal connecting hole.

9. The bonding device as claimed in claim 1, wherein:
the elastic member has a plurality of first wires;
the second bonding structure further includes a second wire connecting member having a plurality of third connectors, each of which has a third connecting slot and a plurality of third mechanical contacts, and a second bonding member including a plurality of fourth mechanical contacts;
the first bonding structure further includes a second signal connecting line having a plurality of second wires being respectively inserted into the plurality of third connecting slots to electrically connect the second wire connecting member;
the plurality of third mechanical contacts are respectively inserted into the plurality of fourth mechanical contacts to mechanically connect the second bonding member;
the second bonding structure is detachably fitted to a relatively stable portion of a user, and the stable portion includes at least one of a shoulder, a chest, a back and a waist;
the second bonding member further includes a plurality of positioning protrusions;
the plurality of third connectors are configured to mechanically connect to the second bonding member according to the plurality of positioning protrusions;
each of the plurality of third connectors is a conductor connector, and the plurality of positioning protrusions are respectively a plurality of insulator protrusions;
the plurality of third mechanical contacts include a plurality of via holes, and the plurality of fourth mechanical contacts include a plurality of fixing protrusions;
the plurality of fixing protrusions respectively penetrate the plurality of via holes to mechanically connect to the plurality of third connectors; and
each of the third connectors further has a recess and the plurality of first electrical contacts located at the bottom of the recess.

10. The bonding device as claimed in claim 1, wherein:
the second bonding structure further includes a rigid unit having a plurality of second electrical contacts electrically connected to the plurality of first electrical contacts respectively to enable the rigid unit electrically connected to the first wire connecting member;
at least one of the plurality of second electrical contacts is used to form a conduction or a disconnection, wherein the conduction or the disconnection is used to determine a wearing position of the rigid unit;
the rigid unit is a signal processing module;
the second bonding structure is combined with the first bonding structure to form the bonding device; and
the first signal connecting line further includes a signal connector, and the first bonding structure includes a signal connecting hole for being electrically connected to the signal connector.

11. A bonding structure (24) for a wearable device (10), comprising:
a wire connecting member (N5-H) including a plurality of connectors (N51-H), each of which has a plurality of first mechanical contacts (N55-H, N56-H), and a plurality of slots (N52-H);
a bonding member (N4) including a plurality of second mechanical contacts (N45, N46); and
a signal connecting line (P2_2) having a plurality of first wires (P10), wherein:

the plurality of first wires (P10) are respectively electrically connected to the plurality of slots (N52-H) for electrical connection to the wire connecting member (N5-H); and
the plurality of first mechanical contacts (N55-H, N56-H) respectively inserted into by the plurality of second mechanical contacts (N45, N46) for mechanical connection to the bonding member (N4).

12. The bonding device as claimed in claim 11, wherein:
the bonding structure is detachably fitted to a relatively stable portion of a user, and the stable portion includes at least one of an arm, a leg, a chest, a back and a waist;
the bonding member further includes a plurality of positioning protrusions;
the plurality of connectors (N51-H) are configured to mechanically connect to the bonding member through the plurality of positioning protrusions;
each of the plurality of connectors is a conductor connector, and the plurality of positioning protrusions are respectively a plurality of insulator protrusions;
the plurality of first mechanical contacts include a plurality of via holes, and the plurality of second mechanical contacts include a plurality of fixing protrusions;
the plurality of fixing protrusions respectively engage with the plurality of via holes to mechanically connect to the plurality of connectors; and
each of the plurality of connectors further has a recess (N57-H) and a plurality of third electrical contacts (N53-H, N54-H) located at a bottom surface of the recess.

13. The bonding device as claimed in claim 11, wherein:
the wire connecting member has the plurality of third electrical contacts;
the bonding structure further comprises a rigid unit having a plurality of fourth electrical contacts respectively electrically connected to the plurality of third electrical contacts to electrically connect the rigid unit to the wire connecting member;
at least one of the plurality of fourth electrical contacts is used to form a conduction or a disconnection, wherein the conduction or the disconnection is used to determine a wearing position of the rigid unit;
the rigid unit is a signal processing module; and
the bonding structure is combined with another bonding structure to form a combination device, wherein the signal connecting line further includes a signal connector, and the another bonding structure includes a signal connecting hole for being electrically connected to the signal connector.

14. A node device for forming a sensing point on a first signal connecting line of a wearable device, wherein the first signal connecting line has a plurality of signal wires, and is used for being connected to a sensing module to form the sensing point, and the node device comprises:
a wearable device body; and
a first bonding structure including a first wire connecting member and an elastic member having a plurality of first wires, wherein the first wire connecting member includes:
a plurality of first connectors disposed on the wearable device body, each of the plurality of first connectors has a plurality of first mechanical contacts and a plurality of first connecting slots; and
a plurality of first electrical contacts are respectively disposed on the plurality of first connectors, and electrically connected to the plurality of signal wires to form the node device, wherein the plurality of first wires are respectively inserted into the plurality of first connecting slots for being electrically connected to the first wire connecting member.

15. The node device as claimed in claim 14, wherein:
the node device is a bonding device for forming a wearable device, and includes the first bonding structure;
the first bonding structure has the first wire connecting member, a plurality of first mechanical structures configured to form a first mechanical bond and the plurality of first electrical contacts configured to form a first electrical bond, and including:
a first bonding member; and
an elastic member; and
a second bonding structure including the first signal connecting line, wherein:
the first wire connecting member, the first bonding member, and the elastic member form the first mechanical bond through the plurality of first mechanical structures;
the first wire connecting member, the first bonding member, and the elastic member form the first electrical bond through the plurality of first electrical contacts; and
the elastic member is electrically connected to the plurality of signal wires to combine the first bonding structure and the second bonding structure.

16. The node device as claimed in claim 15, wherein:
the first bonding member includes a plurality of second connectors, each of which has a plurality of second mechanical contacts;
the plurality of first mechanical structures include the plurality of first connectors, the plurality of second connectors, the plurality of first mechanical contacts and the plurality of second mechanical contacts; and
the plurality of first mechanical contacts are respectively inserted into the plurality of second mechanical contacts, such that the plurality of first connectors are respectively inserted into the plurality of second connectors for being mechanically connected to the first bonding member.

17. The node device as claimed in claim 15, wherein:
the first bonding structure is configured to be worn on an active portion of a user;
the active portion includes at least one of limbs, head, neck, body and hips;
the elastic member is an elastic fabric member, and includes a plurality of elastic fabrics and a plurality of first wires, wherein the plurality of first wires are attached on the plurality of elastic fabrics respectively;
the plurality of first wires are evenly spaced, wavy and flexible;
each of the plurality of first connectors is a conductor connector, and each of the plurality of second connectors is an isolator;
the plurality of second connectors have a plurality of second connecting slots respectively; and
the plurality of first wires are respectively inserted into the plurality of second connectors for mechanical connection to the first bonding member.

18. The node device as claimed in claim 15, wherein:
the plurality of first mechanical contacts respectively include a plurality of via holes, and the plurality of second mechanical contacts respectively include a plurality of protrusions respectively inserted into the plurality of via holes for connection to the plurality of first connectors;
each of the plurality of first connectors has a concave portion and the plurality of first electrical contacts located at a bottom surface of the concave portion;
each of the plurality of second connectors has a protruding portion having a top thereof provided with an upper connector hole and a lower connector hole;
each of the plurality of protruding portions is inserted into the respective concave portion; and
the plurality of first electrical contacts are a pair of contacts respectively mechanically connected to the upper connector hole and the lower connector hole such that the plurality of first connectors and the plurality of second connectors are respectively connected mechanically.

19. The node device as claimed in claim 15, wherein:
the first wire connecting member includes the plurality of first electrical contacts;
the first bonding structure further comprises a rigid unit having a plurality of second electrical contacts electrically connected to the plurality of first electrical contacts to electrically connect the rigid unit to the first wire connecting member;
at least one of the plurality of second electrical contacts is used to form a conduction or a disconnection for determining a wearing position of the rigid unit;
the rigid unit is a motion sensing module; and
each of the plurality of second connectors further includes a plurality of holes, wherein the plurality of first electrical contacts are respectively coupled to the plurality of holes and the plurality of second electrical contacts such that the rigid unit is fixed to the first bonding member.

20. The node device as claimed in claim 15, wherein:
the elastic member has a plurality of first wires;
the second bonding structure further includes a second wire connecting member having a plurality of third connectors, each of which has a third connecting slot and a plurality of third mechanical contacts, a plurality of positioning protrusions and a second bonding member having a plurality of fourth mechanical contacts;
a second signal connecting line has a plurality of second wires;
the plurality of second wires are respectively inserted into the plurality of third connectors for electrical connection to the second wire connecting member;
the plurality of third mechanical contacts are respectively inserted into the plurality of fourth mechanical contacts for mechanical connection to the second bonding member;
the second bonding structure is detachably fitted to a relatively stable portion of a user, in which the stable portion includes at least one of a shoulder, a chest, a back and a waist;
the plurality of third connectors are configured to mechanically connect to the second bonding member through the plurality of positioning protrusions;
each of the plurality of third connectors is a conductor connector;
the plurality of positioning protrusions are respectively a plurality of insulator protrusions;
the plurality of third mechanical contacts include a plurality of via holes;
the plurality of fourth mechanical contacts include a plurality of protrusions;
the plurality of protrusions respectively engage with the plurality of via holes for mechanical connection to the plurality of third connectors;

each of the plurality of third connectors further has a recess and the plurality of first electrical contacts located at a bottom surface of the recess;

the second bonding structure further includes a rigid unit having a plurality of second electrical contacts electrically connected to the plurality of first electrical contacts respectively to enable the rigid unit electrically connected to the first wire connecting member;

at least one of the plurality of second electrical contacts is used to form a conduction or a disconnection, wherein the conduction or the disconnection is used to determine a wearing position of the rigid unit;

the rigid unit is a signal processing module;

the second bonding structure is combined with the first bonding structure to form the bonding device;

the first signal connecting line further includes a signal connector; and the first bonding structure includes a signal connecting hole for electrical connection to the signal connector.

* * * * *